United States Patent

Foell et al.

[11] 4,089,946
[45] May 16, 1978

[54] CLAUDOGENIC-INTERCEPTIVE NONAPEPTIDES

[75] Inventors: Theodore J. Foell, King of Prussia; Richard W. Rees, Bryn Mawr, both of Pa.

[73] Assignee: American Home Products Corporation, New York, N.Y.

[21] Appl. No.: 693,679

[22] Filed: Jun. 7, 1976

[51] Int. Cl.² .................. C07C 103/52; A61K 37/00
[52] U.S. Cl. ........................ 424/177; 260/112.5 LH
[58] Field of Search ............... 260/112.5 LH; 424/177

[56] References Cited

U.S. PATENT DOCUMENTS 3,992,365  11/1976  Beddell et al. ............. 260/112.5 LH
3,992,530  11/1976  Foell et al. ................. 260/112.5 LH

OTHER PUBLICATIONS

Biochem. & Biophysical Research Communication 57, (1974), 335–338, 1248–1256.
D. H. Coy et al., Biochemical and Biophysical Research Communication 67, No. 2, (1975), pp. 576–583.

Primary Examiner—Delbert R. Phillips
Attorney, Agent, or Firm—Richard K. Jackson

[57] ABSTRACT

Compounds of the formula:

L-p-Glu-L-His-L-Trp-L-Ser-L-Tyr-X-Y-L-Arg-L-Pro-NHC$_2$H$_5$ in which X is D-Trp or D-2-(1,4-cyclohexadienyl)Gly Y is L-(N-methyl)-Leu or L-(N-methyl)-ILe or a nontoxic acid addition salt thereof, are potent ovulation inducers and claudogenic-interceptive agents useful in preventing or terminating pregnancy in mammals.

4 Claims, No Drawings

CLAUDOGENIC-INTERCEPTIVE NONAPEPTIDES

BACKGROUND OF THE INVENTION

Many analogues of LRH have been recently produced and tested as agents for ovulation induction. Modification of the amino acid sequence of LRH has been most advantageous to date with removal of the Gly[10] group and production of the Pro-NHC$_2$H$_5$ terminus, providing a compound reportedly three to five times as active as LRH itself. Fujino et al., Biochem. Biophys. Res. Commun. 49 863 (1972). D-Ala[6]-LRH was subsequently shown to be more potent than LRH, by Monahan et al., Biochemistry 12 4616 (1973). Various other D-amino acids have been inserted in 6-position of LRH and des-Gly[10]-Pro-NHC$_2$H$_5$-LRH to produce products with improved ovulation inducing properties. U.S. 3,913,412 and Vilchez-Martinez et al., Biochem. Biophys. Res. Commun. 59 1226 (1974). The potency of D-Ala[6], des-Gly[10]-LRH ethylamide was reported by Coy et al., Biochem. Biophys. Res. Commun. 57 335 (1974) to be about twice that of D-Ala[6]-LRH in stimulating LH secretion. Ling et al., Biochem. Biophys. Res. Commun. 63 801 (1975) report the synthesis and biological activity of D-Ala[6], (N$\alpha$-Me)Leu[7]-LRH in stimulating the secretion of LH, which was found to possess 560% of LRH's potency, placing it in the same potency range as D-Ala[6]-LRH.

DESCRIPTION OF THE INVENTION

In accordance with this invention there is provided a group of novel nonapeptides of the formula:

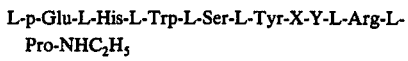

in which

X is D-Trp or D-2-(1,4-cyclohexadienyl)Gly and

Y is L-(N-methyl)Leu or L-(N-methyl)Tle or a non-toxic acid addition salt thereof. Of these compounds, [D-Trp[6],(N-methyl)Leu[7], des-Gly-NH$_2$[10], Pro-ethylamide]LRH is the preferred species from its activity standpoint. These compounds induce ovulation in animals and are claudogenic-interceptive agents useful in preventing or terminating pregnancy in mammals. In the use aspect of this invention, the compounds act as claudogenic-interceptive agents when administered post-coitally to a female mammal after ovulation, in that they disrupt the normal physiological processes necessary for implantation and/or maintenance of a fertile ovum.

The intermediates employed in the production of the nonapeptides of this invention form an additional aspect of the invention. The intermediates are the fully protected polypeptideresin and the fully protected polypeptide ethylamides of the formula:

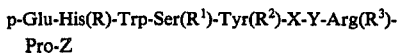

in which

Z represents the —OCH$_2$[polystyrene resin support] or —NHC$_2$H$_5$,

X and Y are defined, supra:

R is a protecting group for the imino nitrogen of the histidyl moiety and R$^3$ is a protecting group for the the guanyl function of the arginyl moiety selected from tosyl, acetyl, benzoyl, tert-butyl, trityl, benzyl, benzyloxycarbonyl and adamantyloxycarbonyl. The tosyl group is preferred as the protecting group for both R and R$^3$. However, the guanyl group of the arginyl moiety may be protected via the N$^{107}$ or N$^{\omega 1}$ nitrogen atoms by the nitro or tosyl protecting groups and via the N$^\delta$ nitrogen atom or either of the N$^w$ or N$^{w1}$ nitrogen atoms by benzyloxycarbonyl, adamantyloxycarbonyl or trityl group; and R$^1$ and R$^2$ are protecting groups for the hydroxyl groups of serine and tyrosine. The hydroxyl protecting groups conventionally employed for this purpose are acetyl, tosyl, benzoyl, tert-butyl, trityl, benzyl, benzyloxycarbonyl, 2,6-dichlorobenzyl, and the like, the benzyl and 2,6-dichlorobenzyl groups being preferred for this purpose.

The nonapeptides of this invention are prepared by solid phase methodology, following techniques generally known in the art for building an amino acid sequence from an initial resin supported amino acid. Merrifield, J.A.C.S. 85, 2149 (1963) generally illustrates the technique involved.

The resin support employed may be any suitable resin conventionally employed in the art for the solid phase preparation of polypeptides, preferably polystyrene which has been crosslinked with from 0.5 to about 3-percent divinyl benzene, which has been chloromethylated to provide sites for ester formation with the initially introduced protected amino acid. The amino protected proline is coupled to the chloromethylated resin according to the procedure of Gisin, Helv. Chim. Acta., 56, 1476 (1973). Following the coupling of the amino protected proline to the resin support, the amino protecting group is removed by standard methods employing trifluoroacetic acid in methylene chloride, trifluoroacetic acid alone or HCl in dioxane. The deprotection is carried out at a temperature between about 0° C. and room temperature. After removal of the amino protecting group the remaining α-amino protected and, if necessary, side chain protected amino acids are coupled, seriatim, in the desired order to obtain the product. Alternatively, multiple amino acid group may be coupled by the solution method prior to coupling with the resin supported amino acid sequence. The selection of an appropriate coupling reagent is within the skill of the art. A particularly suitable coupling reagent is N,N'-diisopropyl carbodiimide. Another applicable coupling agent is N,N'-dicyclohexylcarbodiimide.

Each protected amino acid or amino acid sequence is intorduced into the solid phase reactor in a two to six fold excess and the coupling is carried out in a medium of dimethylformamide: methylene chloride or in either dimethylformamide or methylene choride alone. In cases where incomplete coupling occurs the coupling procedure is repeated before removal of the α-amino protecting group, prior to introduction of the next amino acid to the solid phase reactor. The success of the coupling reaction at each stage of the synthesis is monitored by the ninhydrin reaction as described by E. Kaiser et al., Analyt. Biochem, 34, 595 (1970).

The necessary α-amino protecting group employed for each amino acid introduced into the polypeptide is preferably tert-butyloxycarbonyl, although any such protecting group may be employed as long as it is not removed under coupling conditions and is readily removed selectively in relation to the other protecting groups present in the molecule under conditions which otherwise do not effect the formed molecule. Additional examples of such α-amino protecting groups from which selection may be made, after consideration of the rest of the polypeptide molecule, are trityl, phthalyl, tosyl, allyloxycarbonyl, cyclopentyloxycarbonyl, tert-amyloxycarbonyl, benzyloxycarbonyl, o or p-nitrobenzyloxycarbonyl and the like.

The criterion for selecting protecting groups for R–R³ are (a) the protecting group must be stable to the reagent and under the reaction conditions selected for removing the α-amino protecting group at each step of the synthesis, (b) the protecting group must retain its protecting properties (i.e. not be split off under coupling conditions), and (c) the protecting group must be readily removable upon conclusion of the polypeptide synthesis, under conditions that do not otherwise effect the polypeptide structure.

The fully protected, resin supported nonapeptides present the amino acid sequence:

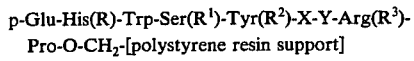

in which the group -O-CH₂-[polystyrene resin support] represents the ester moiety of one of the many functional groups present in the polystyrene resin.

The fully protected nonapeptides are removed from their resin support by treatment with ethylamine at room temperature followed by removal of any excess ethylamine to yield the intermediate.

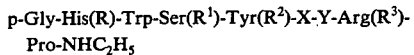

The fully protected intermediate described in the preceding paragraph is deprotected with liquid hydrogen fluoride in the presence of anisole to yield the nonapeptide claudogenic-interceptive agents of this invention.

The acid addition salts of the nonapeptides of this invention are produced by known techniques from either inorganic or organic acids known to afford pharmaceutically acceptable non-toxic addition products, such as hydrochloric, hydrobromic, sulfuric, phosphoric, maleic, acetic, citric, benzoic, succinic, malic, ascorbic acid, and the like.

The claudogenic-interceptive agents of this invention, when administered to a female mammal, post-coitally pursuant to a daily regimen of at least about 3 micrograms per day per kilogram host body weight for a period of at least three days, completely prevent pregnancy.

Although applicants do not wish to be bound by any specific theory of activity, they propose and believe, based upon studies conducted with a variety of animal models, that the nonapeptides of this invention exert a claudogenic/interceptive action via stimulation of the hypophysical-ovarian steroid axis.

In any event, regardless of the physiological pathway to the end result, the nonapeptides of this invention effectively prevent pregnancy in female mammals upon administration after coitus.

Hence the nonapeptides of this invention are useful as "morning-after" contraceptives to prevent or terminate pregnancy in the female mammal. Within this context, the nonapeptides may be used as anti-littering agents for control of rodent populations without use of redenticides and their possible undesirable effect on other animals in the environment.

Pregnancy was avoided in the animal models by daily administration of the nonapeptide of this invention during the day 1 to day 7 period after coitus as well as upon daily administration over the day 7 to day 12 period, post coitus. Thus both a claudogenic (pre-implantation) as well as an interceptive (post-implantation) type of interference with pregnancy was established.

The procedure followed in evaluating the anti-gravidity properties of the nonapeptides of this invention was as follows: Mature, female, Sprague-Dawley rats (350 + 30 grams body weight) maintained on a 14:10 light:dark schedule were caged with fertile male rats on the evening of proestrus. The presence of vaginal sperm the next morning was considered day 1 of pregnancy. The nonapeptide ethylamine produced in the following examples, representative of the entire group of compounds of this invention, was administered subcutaneously in a corn oil vehicle on days 1–7, or 7–12 of pregnancy at a rate of as low as 1 μg/rat/day. One-half the daily dose was administered at 9 A.M. and at 3 P.M. each day. The recipients of day 1–7 treatment were autopsied on day 14. The recipients of day 7–12 treatment were autopsied on day 18 of pregnancy. The effectiveness of the ethylamide and its effective dose was established by the absence of uterine implantation sites and fetuses. The presence of at least one normal fetus was considered to be the criterion for pregnancy. The claudogenic/interceptive activity of the nonapeptides of this invention was thereby established at a daily dose as low as about 3 micrograms per kilogram host body weight, the treatment being 100 percent effective at a dose of 1 microgram per rat per day in a five rat sample for the day 1–7 period and 10 micrograms for the day 7–12 period.

For the purpose of defining the post coital stages of pregnancy in the rat as an experimental model, the following schedule is provided in definition of post-coital contraceptive activity which, for the purpose of this disclosure, is intended to embrace both pre-(claudogenic) and post-(interceptive) implantation contraceptive activity; day 1 — vaginal sperm; days 1–3 — ova transport in oviducts, fertilization; days 3–5 — blastocyst free in uterine lumen; days 5–7 — implantation into uterine wall; days > 7 — post implantation.

Based upon the findings of activity in the prevention of development of pregnancy in the rat model and the fact that present evidence indicates that the hormonal situation relating to the reproductive cycle up to and including ovulation, is basically the same in all female vertebrates, e.g. the human reproductive cycle is physiologically analogous with that of the rat, the activity of the nonapeptides of this invention effectively interferes with the development of the blastocyst pre- and post-implantation in the uterus in all mammals, including the human.

Thus, in accordance with the use aspect of this invention there is provided a method for preventing pregnancy in a mammal which comprises administering:

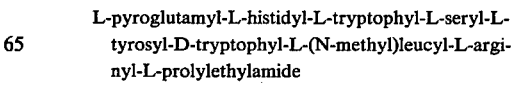

or

L-pyroglutamyl-L-histidyl-L-tryptophyl-L-seryl-L-tyrosyl-D-2-(1,4-cyclohexadienyl)glucyl-L-(n-methyl)leucyl-L-arginyl-L-prolylethylamide or the (n-methyl)isoleucyl[7] analogue of either compound, to said mammal, post coitally, in a daily regimen containing at least about 3 micrograms per kilogram host body weight for a period sufficient to terminate said pregnancy. In operation, the anti-gravidity compounds of this invention interfere with the mechanism of gestation, whether that interference is by an early post-coital, pre-implantation contraceptive or by a postimplantation interceptive mechanism. Hence, the effective sequence of daily administration in the human is from day 1 of ovulation-fertilization to about day 6 to produce a claudogenic response, or from day 6 to about day 14 post ovulation — fertilization to effect an interceptive response in the gestational period. The human dose, based upon the posology of the experimental model, is approximately 1.5 milligrams per day for a 50 kilogram female. For practical purposes, the applicable subcutaneous human dose is about 50 μg/kg/day or 2.5 mg/50 kg female for a claudogenic effect and about 500 μg/kg/day or 25 mg/50 kg female/day for an interceptive effect.

The nonapeptides of this invention may be administered in any convenient form, orally or parenterally, with or without conventional pharmaceutical adjuvants well known to the art. In addition, conventional adducts of the nonapeptides may be employed to prolong their effectiveness, such as the protamine zinc or aluminum adducts which are parpared by conventional techniques.

The ovulation-induction properties of the nonapeptides of this invention was determined with the preferred compound, [D-Trp[6],(N-methyl)Leu[7],des-Gly-NH$_2$[10],Pro-ethylamide]LRH as follows: Proestrous female Sprague-Dawley rats were injected intraperitoneally with a hypnotic dose of Nembutal ® (50 mg/kg) at 1:30 PM. Between 1:40 and 1:50 PM the rats received the test material via the jugular vein. The following morning the animals were sacraficed and the fallopian tubes examined for ova under a dissecting microscope. The results of this test demonstrated ovulation inducing activity in 100 percent of the rats at a dose of 0.1 mg per rat, in comparison with LRH which requires about 3 mg per rat to obtain 100 percent ovulation and [D-Ala[6],des-Gly-NH$_2$[10], Proethylamide]LRH which requires about 1 mg per rat for the same response. Thus, in its ovulation induction, the preferred compound of this invention is about ten times as active as its closest structural analogues.

The following examples illustrate the preparation of p-Glu-His-Trp-Ser-Trp-D-Trp-(N-methyl)Leu-Arg-Pro-NHC$_2$H$_5$ which is the preferred claudogenic-interceptive agent of this invention. It is to be understood, that the other nonapeptides disclosed herein are prepared in the same manner by merely substituting the indicated specific amino acid into the preparatory sequence at the proper position. Thus, the examples are illustrative rather than limiting in nature.

EXAMPLE 1

Preparation of tert-butyloxycarbonylproline resin (method of Gisin, Helv. Chim. Acta, 56, 1476[1973])

Tert-Butyloxycarbonylproline (18.56 g., 86.3 m moles) in an ethanol (112 ml.) — water (48 ml.) mixture was treated with concentrated aqueous cesium hydrogen carbonate solution until the pH of the solution reached 7. The reaction mixture was stripped and dried by repeated stripping using ethanol, ethanol-benzene, benzene (three times). The residue was dried over phosphorous pentoxide, in vacuo at room temperature overnight.

The total product in dimethylformamide (880 ml.) was stirred overnight at 50° C, under nitrogen, with 80 g. of Bio-Beads S.X. 1 Resin (chloromethylated capacity 0.89 meq./g.). The filtered resin was washed thoroughly with dimethylformamide (twice), dimethylformamide-10% water (twice), dimethylformamide (twice), methanol (twice), chloroform (thrice) and dried over P$_2$O$_5$. Amino acid analysis indicated a substitution on the resin of 0.56 meq./g.

EXAMPLE 2

L-Pyroglutamyl-N$^{im}$-tosyl-L-histidyl-L-tryptophyl-O-benzyl-L-seryl-O-(2,6-dichlorobenzyl)-L-tyrosyl-D-tryptophyl-N-methyl-L-leucyl-N$^g$-tosyl-L-arginyl-L-prolyl acyl resin ester

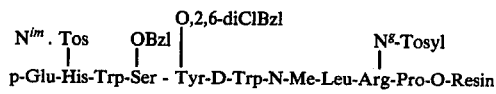

The tert-butyloxycarbonylprolin resin (4.725 g) from Example 1 was placed in a Beckman 990 peptide synthesizer and treated as follows:
1. Wash with methanol.
2. Wash with methylenechloride.
3. Wash with methanol (two times).
4. Wash with methylenechoride (two times)
5. Prewash with 1:1 trifluoroacetic acid-methyl chloride (v/v) containing 0.5% dithioerythritol.
6. Deprotection with the solvent from step 5 (two times for 15 minutes each).
7. Wash with methylenechloride.
8. Wash with dimethylformamide.
9. Wash with 12.5% triethylamine in dimethylformamide (v/v) for 10 minutes (two times).
10. Wash with dimethylformamide.
11. Wash with methylene chloride (two times)
12. Wash with methanol (two times).
13. Wash with methylene chloride (three times).
14. The peptide resin is then gently stirred with 9 moles of the desired tert-butyloxycarbonyl amino acid in ca. 30 ml. of a 1:1 dimethylformamide-methylene chloride (v/v) solvents.
15. 1M diisopropylcarbodiimide (DIC) in methylene chloride (10 m moles) is added in two portions over 30 minutes.
16. The reaction mixture is stirred for 7 hours.

A contact time of 1.5 minutes is allowed for each step unless otherwise stated.

The above steps are repeated until all of the desired amino acids are added.

The following amino acid residues were then introduced consecutively: t-Boc-N$^g$-tosyl-L-arginine (9 m mole), t-Boc-N-methyl-L-Leucine (9 m moles), t-Boc- D-tryptophan (9 m moles), then without deblocking a second portion of t-Boc-D-tryptophan (9 m moles) was allowed to react. Then resuming the normal sequence t-Boc-2,6-dichloro-benzyl-L-tyrosine (9 m moles), t-Boc-O-benzyl-L-serine (9 m moles), t-Boc-L-tryptophan (9 m moles), t-Boc-im-tosyl-L-histidine (9 m moles), and L-2-pyrrolidone-5-carboxylic acid (9 m moles) were added. The washed peptide resin was dried in vacuo and weighed 8.422 g.

EXAMPLE 3

L-pyroglutamyl-N$^{im}$-tosyl-L-histidyl-L-tryptophyl-O-benzyl-L-seryl-O-(2,6-dichlorobenzyl)-L-tyrosyl-D-tryptophyl-N-methyl-L-leucyl-N$^g$-tosyl-L-arginyl-prolinethylamide Protected peptide-resin (8.422 g) from Example 2 and ethylamine (120 ml.) were stirred overnight in a glass pressure bottle. Ethylamine was removed under reduced pressure and the residue washed with methanol, dimethylformamide (four times), methanol and methylene chloride. The combined filtrates were evaporated in vacuo below 35° C. to give the title compound (3.277 g).

EXAMPLE 4

L-pyroglutamyl-L-histidyl-L-tryptophyl-L-seryl-L-tyrosyl-D-tryptophyl-N-methyl-L-leucyl-L-arginyl-L-prolinethylamide The product of Example 3 was treated in vacuo with anhydrous liquid hydrogen fluoride (120 ml.) and anisole (35 ml.) for 50 minutes at 0° C. Hydrogen fluoride was removed under reduced pressure and the residue distributed between diethyl ether and 10% aqueous acetic acid. Lyophyllization of the acid layer afforded the crude title product (2.404 g.).

EXAMPLE 5

Purification and characterization of L-pyroglutamyl-L-histidyl-L-tryptophyl-L-seryl-L-tyrosyl-D-tryptophyl-N-methyl-L-leucyl-L-arginyl-L-prolin-ethylamide The crude peptide (2.404 g.) in a minimum volume of 0.2N acetic acid was applied to a column of Bio Gel P-2 previously equilibrated with 0.2N acetic acid and then eluted with the same solvent. Fractions of 9 ml. each were collected. Peptide material was located by Ehrlich spot test and UV analysis. One major fraction was obtained, 34 50 (2.234 g.). A second Bio Gel P-2 column afforded 1.928 g. of desired material. This material was rechromatographed on a partition column of Sephadex G-25 fine (2.5 × 100 cm.) prepared by equilibration with lower phase and then upper phase of the BAW system (n-butanol:acetic acid:water, 4:1:5). Elution with upper phase afforded fractions A 36–48 (820 mg.), B 49–64 (633 mg.). Fraction A was rechromatographed using the same system which afforded 295 mg. of the desired peptide.

The Rf value of the peptide (30 μg load) in the thin layer system (silica, plates-Brinkman) n-butanol:acetic acid: water (4:1:5, upper phase). Rf 0.21 n-butanol:acetic acid:ethyl acetate:water (1:1:1:1). Rf 0.57.

The optical rotation measured on a Carl Zeiss LEP A-2 photoelectric precision polarimeter, $[a]_D^{26}$ = −80.91° (c=0.98, 1% acetic acid).

Hydrolysis of the peptide in methanesulfonic acid (0.2 ml/1 mg. peptide) for 20 hours at 110° C. in a closed evacuated system revealed all of the required amino acids to be present.

What is claimed is:

1. The compound of the formula:

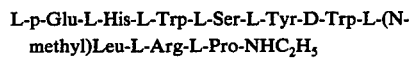

or a non-toxic acid addition salt thereof.

2. A method for terminating pregnancy in a female mammal which comprises administering a nonapeptide of the formula:

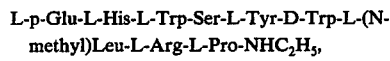

or a pharmaceutically acceptable acid addition salt thereof, to said mammal, post coitally, in a daily regimen containing at least about 3 micrograms per kilogram host body weight for a time sufficient to terminate pregnancy.

3. The method of claim 2 in which said nonapeptide is administered, orally or parenterally, to said mammal following a daily regimen beginning on day one after coitus and extending through about the first eight days post implantation.

4. The method of claim 2 in which said nonapeptide is administered, orally or parenterally, following a daily regimen beginning on day one after coitus and extending through about day seven post coitus.

* * * * *